United States Patent
Brommersma

(10) Patent No.: US 6,645,140 B2
(45) Date of Patent: Nov. 11, 2003

(54) CONTINUOUSLY RINSING DOUBLE-SHEATH ENDOSCOPE

(75) Inventor: Pieter Brommersma, Bargteheide (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 35 days.

(21) Appl. No.: 10/010,804

(22) Filed: Nov. 13, 2001

(65) Prior Publication Data

US 2002/0058859 A1 May 16, 2002

(30) Foreign Application Priority Data

Nov. 15, 2000 (DE) .......................... 100 56 618

(51) Int. Cl.[7] .............. A61B 1/00; A61B 1/12

(52) U.S. Cl. .............. 600/128; 600/105; 600/156; 600/153

(58) Field of Search ............... 600/128, 129, 600/130, 105, 153, 156, 157

(56) References Cited

U.S. PATENT DOCUMENTS

| 4,132,227 | A | * | 1/1979 | Ibe | 600/105 |
|---|---|---|---|---|---|
| 4,630,598 | A | * | 12/1986 | Bonnet | 600/135 |
| 5,509,892 | A | * | 4/1996 | Bonnet | 600/156 |
| 5,637,075 | A | * | 6/1997 | Kikawada | 600/153 |
| 5,807,240 | A | * | 9/1998 | Muller et al. | 600/135 |
| 5,876,329 | A | * | 3/1999 | Harhen | 600/125 |
| 6,358,200 | B1 | * | 3/2002 | Grossi | 600/156 |

* cited by examiner

Primary Examiner—John Mulcahy
Assistant Examiner—Jocelyn Ram
(74) Attorney, Agent, or Firm—Rankin, Hill, Porter & Clark LLP

(57) ABSTRACT

A continuously rinsing double-sheath endoscope, which includes an inner sheath and an outer sheath. The inner sheath includes a feed duct and receives an optics. The outer sheath surrounds the inner sheath and cooperates with the inner sheath to subtend a return flow duct. The outer sheath is fitted at its distal end zone with at least one aperture to establish fluid communication between the return duct and the ambience of the outer sheath. Cross-sectional geometric centers of gravity of the inner and outer sheaths are mutually shifted along most of the length of the return-flow duct subtended between them.

4 Claims, 2 Drawing Sheets

CONTINUOUSLY RINSING DOUBLE-SHEATH ENDOSCOPE

BACKGROUND OF THE INVENTION

1. Field of the Invention

The present invention relates to a double-sheath endoscope having an inner shealth that cooperates with a surrounding outer sheath to define a return duct.

2. Description of Related Art

Endoscopes of the aforementioned type are used, for instance, in the form of urological resectoscopes for transurethral interventions, in particular with respect to prostate resection. Such resectoscopes comprise an inner sheath containing the optics and, for instance, to support an axially displaceable and cutting resection loop. The remaining free lumen of the inner sheath is configured as a feed duct for the rinsing liquid. Rinsing liquid is fed from the feed duct above the distal end of the optics to cleanly flush the area of surgery and to assure a clear view.

Instruments of this kind are also fitted with an outer sheath to attain continuous rinsing, the outer sheath enclosing the inner sheath and together with it subtending a return duct. The outer sheath and/or the inner sheath, if desired, can be rotary. By means of apertures in the distal zone of the outer sheath, the return duct hydraulically or fluidly communicates with the endoscope ambience and serves to return the introduced rinsing liquid.

In a continuous rinsing operation, the rinsing liquid arriving from the proximal side passes at the distal end of the inner sheath, for instance, into the bladder or the uterus and is emptied from there through apertures in the outer sheath's distal zone into the return duct between the outer and inner sheaths to be drained toward the proximal side.

Illustratively as regards resecting, there is danger however that the rinsing liquid should be flushed into the patient's blood circulatory system. The consequences may be dangerous. Furthermore, the amount of liquid entering the circulatory system also increases with increasing bladder pressure. Accordingly, the bladder pressure must be minimized as much as possible. On the other hand, intensive rinsing is required to maintain a clear view of the zone of surgery.

The problem of bladder pressure is compounded by the possible constriction of the return duct. As a results there will be an undesired increase in bladder pressure and, thereby. an increased penetration of the rinsing liquid into the circulatory system.

Implements monitoring the back-and-forth flows of the rinsing liquid are known with which to control these rinsing liquid problems. However, such procedures are both complex and, sometimes, unreliable.

Another solution might be to improve the return flow by increasing the cross-section of the return flow duct. The rinsing liquid then would be drained more rapidly and the return duct would constrict less. The bladder pressure would stay low. However, with the required dimensions of the inner sheath, the outside diameter of the outer sheath then necessarily would be increased. On the other hand, the outside diameter of the instrument always should be minimized to stress the patient as little as possible. With given dimensions of the outer diameter, one might reduce the size of the inner sheath to improve the return flow. But difficulties arise because the optics and, for instance, a surgical implement are contained in this inner sheath and at the same time the lumen must still be sufficient to allow introducing the rinsing liquid.

SUMMARY OF THE INVENTION

Accordingly, it is an objective of the present invention to create a double-sheath endoscope functioning with continuous rinsing and minimizing bladder pressure on account of improved return of the rinsing liquid without thereby increasing the instrument's outside diameter.

In accordance with the present invention, the inner and the outer sheaths are configured so that their geometric cross-sectional centers of gravity shall be mutually apart for most of the length of the return duct that is subtended between them. Illustratively, the present invention provides an eccentric configuration of the inner sheath within the outer sheath, both sheaths being cross-sectionally circular.

The inventive configuration attains an asymmetric return duct between the outer and inner sheaths and cross-sectional zones, offering a larger wall separation or spacing than if the cross-sectional centers of gravity were to coincide. Because the flow impedance of a liquid within a tube decreases at a higher mathematical power with increasing wall spacing, the total flow impedance of the return duct will be decreased.

It is true that there are also cross-sectional zones for which the wall spacings are less compared to the case of coincident centers of gravity: however this feature is more than compensated for by the zones of larger wall spacings. Accordingly, if the total cross-section of the return duct remains constant, the eccentric configuration will offer a lower total flow impedance of the return flow. Thus the return flow is made easier and the bladder pressure is reduced over the design of concentric inner and outer sheaths, all other conditions being kept the same. The return flow zone of larger wall spacing also will constrict more slowly. In the invention, the configuration of inner and outer sheaths furthermore allows reduced instrument circumference at constant return-duct flow impedance compared to the coincident design of the state of the art.

The lowering of the total flow impedance in the return duct shall be the larger the greater the mutual shifting of the cross-sectional centers of gravity of the inner and outer sheaths. Accordingly, the minimal total flow impedance shall have been attained when the inner and outer sheaths shall almost touch, the rotatability between inner and outer sheath possibly requiring consideration in such a case.

Moreover, the total flow impedance in the return duct will be the lower, the greater the axial length of the endoscope over which such a cross-sectional shift shall have been implemented. Preferably, the cross-sectional centers of gravity of the inner and outer sheaths therefore shall be shifted over the entire length of the return duct they are subtending.

Alternatively as regards a cross-sectionally egg-shaped, oval outer sheath, the external circumference of the endoscope may be reduced by 1–2 Charriere (French) compared to the circular outer-sheath cross-section at constant flow return performance.

Alternatively as regards a cross-sectionally egg-shaped, oval outer sheath, the external circumference of the endoscope may be reduced by 1–2 charrieres compared to the circular outer-sheath cross-section at constant flow return performance.

Advantageously in accordance with another aspect of the invention and with respect to a cross-sectionally egg-shaped, oval outer sheath, the inner sheath shall be configured within it such that the maximum width of the return duct shall be situated between the inner sheath and the outer sheath zone exhibiting the smallest radius of curvature. In this way too the total flow impedance in the return duct will be decreased relative to alternative configurations because at a given outside diameter and for no other configuration can such a maximum return duct width be attained.

In further accordance with the present invention, and with reference to a double-sheath endoscope comprising an outer-sheath bulge projecting beyond the proximal outer-sheath cross-section, the bulge is mounted in that peripheral zone of the outer sheath which is farthest away from the inner sheath. The bulge is defines apertures implementing fluid communication between the return duct and the surroundings of the outer sheath. The input of rinsing liquid predominantly takes place through these apertures in the bulge of the distal end zone of the outer sheath. On that account the return flow of this design is optimal relative to alternative configurations.

BRIEF DESCRIPTION OF THE DRAWINGS

The invention is elucidated below in relation to illustrative embodiments schematically shown in the attached Figures.

DETAILED DESCRIPTION OF THE PREFERRED EMBODIMENT

Figure 1:
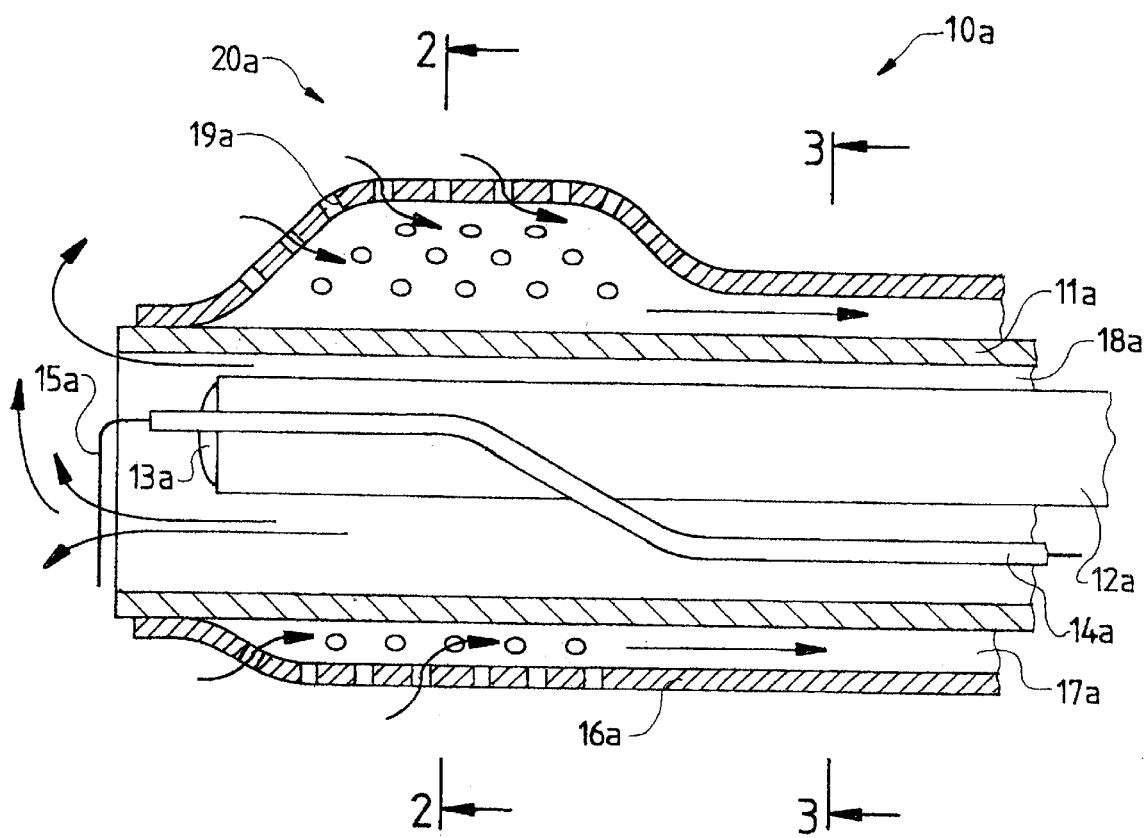
FIG. 1 is a longitudinal section of the distal end zone of a known double-sheath endoscope.
Figure 2:
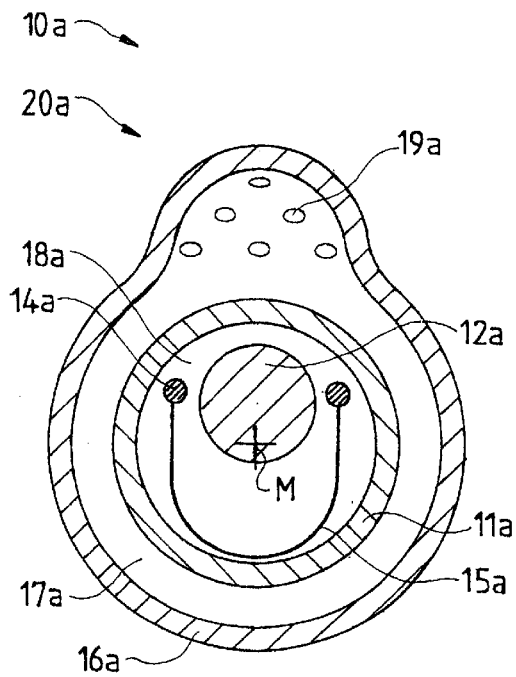
FIG. 2 is a section along line 2—2 of FIG. 1.
Figure 3:
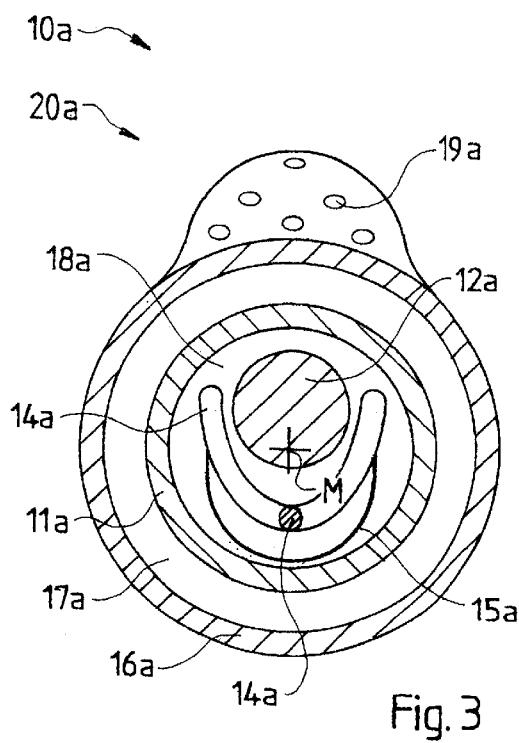
FIG. 3 is a section along line 3—3 of FIG. 1.
Figure 4:
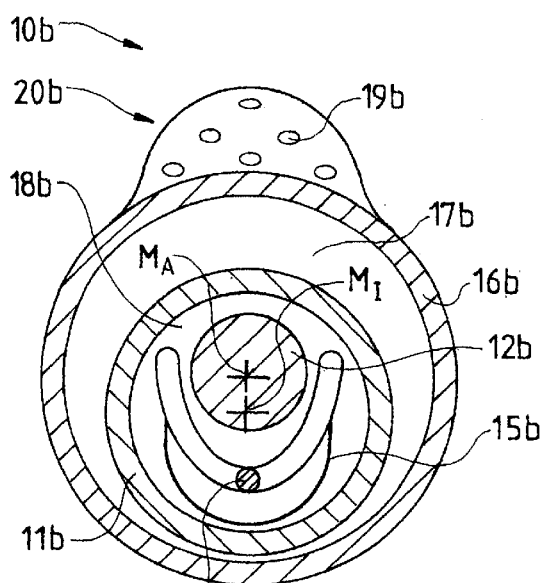
FIG. 4 is a section similar to that of FIG. 3 of a first embodiment of the invention.
Figure 5:
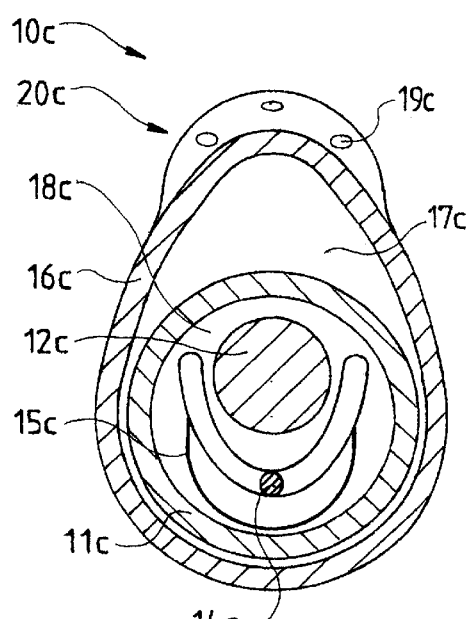
FIG. 5 is a section similar to that of FIG. 4 of a second embodiment of the invention.

FIGS. 1 through 3 show the state of the art and FIGS. 4 and 5 show illustrative embodiments of the invention. The same reference numerals are used in these Figures for functionally identical component, using suffixes "a" for FIGS. 1 through 3 and resp. suffixes "b" and "c" for FIGS. 4 and 5.

FIG. 1 shows the distal end zone of a double-sheath endoscope 10a in the form of a urological resectoscope of the known state of the art. FIG. 2 is a cross-section of this endoscope 10a along the line 2—2. FIG. 3 is a cross-section of this endoscope 10a along the line 3—3.

The inner sheath 11a is enclosed by an outer sheath 16a and together they subtend between them a gap 17a. The configuration of the inner and outer sheaths 11a and 16a is shown in greater detail in FIGS. 2 and 3, respectively.

The inner sheath 11a is enclosed by an outer sheath 16a and together they subtend between them a gap 17a. The configuration of the inner and outer sheaths 11a and 16a resp. is shown in greater detail in FIGS. 2 and 3.

The outer sheath of the endoscope 10a is fitted at its distal end zone with a bulge 20a projecting above the proximal outer-sheath cross-section and comprising apertures 19a for fluid communication between the return duct 17a and the ambience of the outer sheath 16a. The returned rinsing liquid predominantly enters the return duct 17a at this bulge.

As shown in FIG. 3, the inner and outer sheaths 11a and 16a exhibit a circular cross-section except for the above discussed distal zone of the outer sheath 16a fitted with the bulge 20a. The inner sheath 11 a enclosed by the outer sheath 16a is concentric with latter and both comprise an axis of rotational symmetry M. The rotationally symmetrical annular gap 17a is subtended between the outer and inner sheaths 16a and 11a.

Just as is the case for the endoscopes of the invention 10b, 10c discussed further below, the shown known endoscope 10a shall function with continuous rinsing during surgery. The lumen of the inner sheath 11a not occupied by the optics 12a or by a surgical implement 14a serves as the feed duct 18a crossed in normal functioning by the rinsing liquid coming from the proximal side. This rinsing liquid issues at the distal end of the inner sheath 11a into the zone of surgery which it then rinses and in particular it clears the field of view of the objective 13a. The rinsing liquid fed into and through the inner sheath 11a will flow back, i.e. return, through the apertures 19a present in the distal end zone of the outer sheath 16a through which the rinsing liquid illustratively laden with blood or the like may reach the gap 17a between the outer sheath 16 and the inner sheath 11a. Inside the gap 17a, the rinsing liquid then flows toward the proximal side. The gap 17a acts as the return duct. Illustratively, the return flow may be enhanced by means of suction at the proximal side.

FIG. 4 shows a first double-sheath endoscope 10b of the invention, the sectional view of FIG. 4 agreeing with that of FIG. 3. While both the inner sheath 11b and the outer sheath 16b are cross-sectionally circular, on the other hand, and contrary to the endoscope 10aof that kind shown in FIG. 3, in the invention the inner sheath 11b is configured eccentrically to the outer sheath 16b, that is, the axis of rotational symmetry $M_A$ of the outer sheath 16b and axis of rotational symmetry $M_1$ of the inner sheath do not coincide. The gap 17b subtended between the two sheaths 11b, 16b therefore is cross-sectionally asymmetrical and, compared to the known concentric configuration of FIG. 3, this configuration of the invention entails cross-sectional zones of enlarged wall spacings and cross-sectional zones of reduced wall spacings.

Even though the total cross-sectional area of the gap 17b remains the same, the eccentric configuration of the inner sheath 11b inside the outer sheath 16b results in a decrease in flow impedance in the gap 17b acting as the return duct. This result is attained because the flow impedance of a liquid flowing through a tube drops at a raised mathematical power as the wall spacing increases. The increase in flow impedance in cross-sectional zones of reduced wall spacings is over-compensated by the decreases of flow impedance in cross-sectional zones of enlarged wall spacings. The net result is a drop in total flow impedance in the return duct 17b.

The bulge 20b of the outer sheath 16b is situated on that side of the outer sheath 16b which is opposite in direction to the shift of the inner sheath 11b relative to the outer sheath 16b, that is at that site exhibiting the largest space from the inner sheath 11b.

Another illustrative embodiment of a double-sheath endoscope of the invention is shown in FIG. 5, the sectional view coinciding with that of FIGS. 3 and 4.

In FIG. 4 the cross-section of the outer sheath still was circular, but in FIG. 5 the outer sheath 16c exhibits an egg-shaped, oval cross-section. The inner sheath 11c is configured within the egg-shaped, oval outer sheath 16c such that, on one side, the outer sheath 16c encloses the inner sheath 11c with small play and, on the other side, the outer sheath subtends the maximum width of the return duct 17c between the inner sheath 11c and the outer-sheath zone of least radius of curvature.

Alternatively, the outer periphery may be reduced by 1–2 Charriere (French) both when using a cross-sectionally circular outer sheath and an egg-shaped, oval cross-section when maintaining good return-flow properties of known endoscopes. Also the inner sheath may be designed with a cross-section other than circular.

Alternatively, the outer periphery may be reduced by 1–2 charrieres both when using a cross-sectionally circular outer sheath and an egg-shaped, oval cross-section when maintaining good return-flow properties of known endoscopes. Also the inner sheath may be designed with a cross-section other than circular.

If rotatability of the inner sheath within the outer one were desired, then the inner and outer sheaths and the gaps they subtend between them must be designed accordingly. In the case of circular cross-sections both for the inner and the outer sheaths, rotatability shall be unrestricted if the wall spacing is chosen sufficiently large.

What is claimed is:

1. A continuously rinsing, double-sheath endoscope (10b, 10c), comprising an inner sheath (11b, 11c) with a circular cross-section that includes a feed duct (18b, 18c) and receives an optics (12b, 12c) and an instrument (14b, 15b; 14c, 15c), further comprising an outer sheath (16b, 16c) enclosing the inner sheath (11b, 11c) so as to cooperate with the inner shaft to subtend a return flow duct (17b, 17c), a distal end zone of said outer sheath (16b, 16c) defining at least one aperture (19b, 19c) to set up fluid communication between the return duct (17b, 17c) and the outside of the outer sheath (16, 16c), wherein the inner sheath (11b, 11c) and the outer sheath (16b, 16c) are configured such that their particular cross-sectional, geometric centers of gravity are mutually shifted along at least most of the length of the return-flow duct (17b, 17c) subtended between them, and wherein the inner sheath and the outer sheath do not contact each other along their lengths.

2. The double-sheath endoscope (10c) as claimed in claim 1, wherein the outer sheath (16c) has an egg-shaped, oval cross-sectional shape.

3. The double-sheath endoscope (10c) as claimed in claim 2, wherein the inner sheath (11c) is configured, inside the egg-shaped, oval outer sheath (16c), such that the largest spacing between the inner sheath (11c) and the outer sheath (16) is situated between the inner sheath (11c) and a zone of the outer sheath which exhibits a least radius of curvature.

4. The double-sheath endoscope (10b, 10c) as claimed in claim 1, wherein the outer sheath (16c, 16d) defines a bulge (20b, 20c), said bulge being situated at the distal end zone of the endoscope (10b, 10c) and projecting beyond a cross-section of a proximal portion of the outer sheath, said at least one aperture (19b, 19c) being formed in said bulge to set up fluid communication between the return duct (17b, 17c) and outside of the outer sheath (16b, 16c), wherein the bulge (20b, 20c) coincides with a peripheral zone of the outer sheath (16b, 16c) that exhibits a largest spacing from the inner sheath (11b, 11c).

* * * * *

UNITED STATES PATENT AND TRADEMARK OFFICE
CERTIFICATE OF CORRECTION

PATENT NO.    : 6,645,140 B2
DATED         : November 11, 2003
INVENTOR(S)   : Brommersma It is certified that error appears in the above-identified patent and that said Letters Patent is hereby corrected as shown below:

<u>Column 6,</u>
Line 22, after "and" insert -- the --.

Signed and Sealed this

Thirtieth Day of December, 2003

JAMES E. ROGAN
*Director of the United States Patent and Trademark Office*